United States Patent
Sambelashvili et al.

(10) Patent No.: US 9,180,300 B2
(45) Date of Patent: Nov. 10, 2015

(54) LEFT-VENTRICULAR PACING SITE SELECTION GUIDED BY ELECTROGRAM MORPHOLOGY ANALYSIS

(75) Inventors: Aleksandre T. Sambelashvili, Maple Grove, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 160 days.

(21) Appl. No.: 13/598,784

(22) Filed: Aug. 30, 2012

(65) Prior Publication Data

US 2013/0053916 A1  Feb. 28, 2013

Related U.S. Application Data

(60) Provisional application No. 61/528,916, filed on Aug. 30, 2011.

(51) Int. Cl.
| | | |
|---|---|---|
| *A61N 1/00* | (2006.01) | |
| *A61N 1/362* | (2006.01) | |
| *A61B 5/00* | (2006.01) | |
| *A61B 5/0452* | (2006.01) | |
| *A61N 1/368* | (2006.01) | |

(52) U.S. Cl.
CPC .......... *A61N 1/3627* (2013.01); *A61B 5/04525* (2013.01); *A61B 5/7264* (2013.01); *A61N 1/3684* (2013.01); *A61N 1/3686* (2013.01); *A61N 1/362* (2013.01)

(58) Field of Classification Search
CPC ............. A61N 1/00; A61N 1/02; A61N 1/04; A61N 1/05; A61N 1/08; A61N 1/362; A61N 1/365; A61N 1/368; A61N 1/37; A61N 1/372; A61N 1/375; A61N 1/40; A61B 5/04; A61B 5/0402; A61B 5/0408; A61B 5/042; A61B 5/0432; A61B 5/0452; A61B 5/048; A61B 5/05; A61B 5/06
See application file for complete search history.

(56) References Cited

U.S. PATENT DOCUMENTS

| | | | |
|---|---|---|---|
| 5,683,432 A | 11/1997 | Goedeke | |
| 6,393,316 B1 | 5/2002 | Gillberg | |
| 6,442,433 B1 | 8/2002 | Linberg | |
| 6,480,745 B2 | 11/2002 | Nelson | |
| 6,599,250 B2 | 7/2003 | Webb | |
| 6,622,045 B2 | 9/2003 | Snell | |
| 6,978,184 B1 | 12/2005 | Marcus | |
| 7,254,442 B2 | 8/2007 | van Gelder | |

(Continued)

OTHER PUBLICATIONS

Sweeney, MO, et al. "Analysis of ventricular activation using surface electrocardiography to predict left ventricular reverse volumetric remodeling during cardiac resynchronization therapy" Circulation, Jan. 25, 2010, pp. 626-634, vol. 121.

*Primary Examiner* — Christopher D Koharski
*Assistant Examiner* — Elizabeth K So
(74) *Attorney, Agent, or Firm* — Michael C. Soldner

(57) ABSTRACT

A medical device and associated method classify candidate pacing electrode sites for delivering pacing pulses to a patient's heart. A first morphology template is established and stored in memory of the device. A processor is configured to determine a cardiac signal morphology in response to delivering pacing pulses at a candidate pacing site in a first heart chamber. The processor compares the determined cardiac signal morphology to the first morphology template. The pacing site in the first heart chamber is classified in response to the comparing of the determined cardiac signal morphology and the first morphology template.

10 Claims, 6 Drawing Sheets

(56) References Cited

U.S. PATENT DOCUMENTS

| | | |
|---|---|---|
| 7,881,791 B2 | 2/2011 | Sambelashvili |
| 2009/0234415 A1* | 9/2009 | Sambelashvili et al. ........ 607/25 |
| 2010/0152795 A1 | 6/2010 | Schecter |
| 2010/0268059 A1 | 10/2010 | Ryu |

* cited by examiner

LEFT-VENTRICULAR PACING SITE SELECTION GUIDED BY ELECTROGRAM MORPHOLOGY ANALYSIS

CROSS-REFERENCE TO PRIORITY APPLICATION

The present application claims priority and other benefits from U.S. Provisional Patent Application Ser. No. 61/528,916, filed Aug. 30, 2011, incorporated herein by reference in its entirety.

FIELD OF THE DISCLOSURE

The disclosure relates generally to medical devices and, in particular, to a medical device and associated method for selecting the site for electrical stimulation of the heart muscle using comparisons of the morphology of cardiac signals, such as ECG or electrogram (EGM) signals.

BACKGROUND

Cardiac resynchronization therapy (CRT) is a treatment for heart failure patients in which one or more heart chambers are electrically stimulated (paced) to restore or improve heart chamber synchrony. Achieving a positive clinical benefit from CRT is dependent on the location of the pacing site, particularly in the left ventricle (LV). Thus, placement of the pacing leads, especially an LV pacing lead, is important in promoting a positive outcome from CRT. As multi-polar cardiac pacing leads become commercially available, multiple pacing electrode vectors are possible, for example, for pacing in the LV. Guidelines are needed for selecting a lead placement site and for selecting which pacing electrode vector to use for delivering CRT in a most efficacious way. A need remains for efficient, low-cost techniques for reliably determining an optimal lead placement site and pacing vector.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
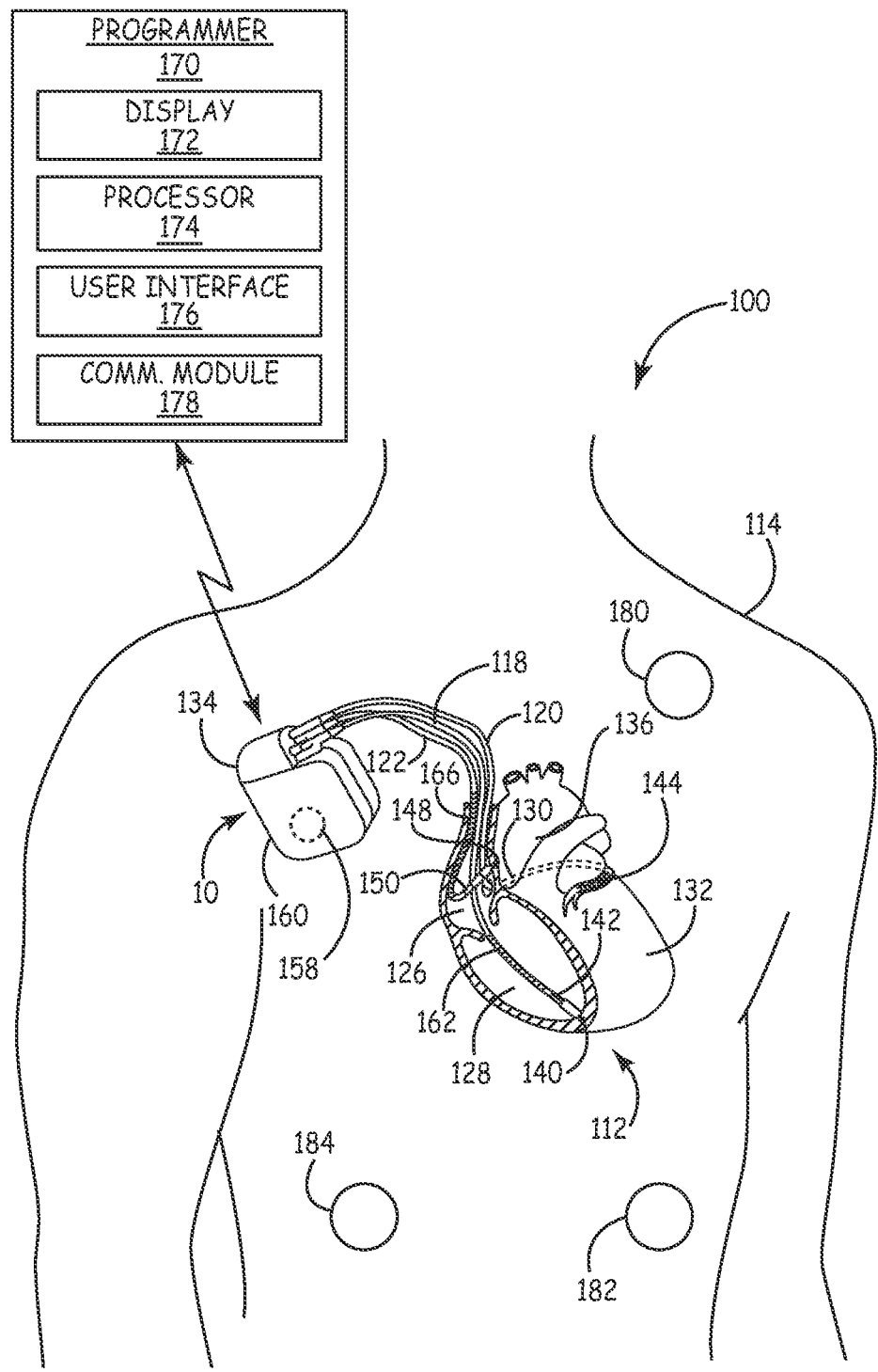
FIG. 1 is a schematic diagram of one embodiment of an implantable medical device (IMD) system in which techniques disclosed herein may be implemented to provide therapy to a patient's heart.

FIG. 1 is a schematic diagram of one embodiment of an IMD system 100 in which techniques disclosed herein may be implemented to provide therapy to a heart 112 of patient 114. System 100 includes IMD 10 coupled to leads 118, 120, and 122 which carry multiple electrodes. IMD 10 is configured for bidirectional communication with programmer 170. IMD 10 may be, for example, an implantable pacemaker, cardioverter, and/or defibrillator that provides electrical signals to heart 112 via electrodes coupled to one or more of leads 118, 120, and 122. IMD 10 is capable of delivering at least single chamber ventricular pacing, and in the embodiment shown, is configured for multi-chamber pacing and sensing in the right atrium (RA) 126, the right ventricle (RV) 128, and the left ventricle (LV) 132 using leads 118, 120 and 122.

IMD 10 delivers RV pacing pulses and senses RV intracardiac EGM signals using RV tip electrode 140 and ring electrode 142 positioned in the RV 128. RV lead 118 is shown to carry a coil electrode 162 which may be used for delivering high voltage cardioversion or defibrillation shock pulses. IMD 10 senses LV EGM signals and delivers LV pacing pulses using the electrodes 144 carried by multipolar coronary sinus lead 120, extending through the RA 126 and into a cardiac vein 130 via the coronary sinus. In some embodiments, coronary sinus lead 120 may include electrodes positioned along the left atrium (LA) 136 for sensing left atrial (LA) EGM signals and deliver LA pacing pulses.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 10 may detect arrhythmias of heart 112, such as fibrillation of ventricles 128 and 132, and deliver defibrillation therapy to heart 112 in the form of electrical pulses. While IMD 10 is shown in a right pectoral implant position in FIG. 1, a more typical implant position, particular when IMD 10 is embodied as an ICD, is a left pectoral implant position.

IMD 10 includes internal circuitry for performing the functions attributed to IMD 10 and a housing 160 encloses the internal circuitry. It is recognized that the housing 160 or portions thereof may be configured as an active electrode 158 for use in cardioversion/defibrillation shock delivery or used as an indifferent electrode for unipolar pacing or sensing configurations. IMD 10 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

In the embodiment shown, IMD 10 is also configured for delivering CRT therapy, which may use a selected pacing vector for LV pacing that includes at least one electrode 144 on multipolar LV lead 120. IMD 10 may be configured to pace in one or both ventricles 128 and 132 for controlling and improving ventricular synchrony. The methods described herein may be implemented in a single, dual or multi-chamber pacemaker or ICD delivering pacing pulses using programmable pacing pulse timing parameters and programmable pacing vectors.

IMD 10 provides EGM signal data to programmer 170 via wireless telemetry. EGM data and/or classifications of one or more pace control parameter settings may be transmitted to programmer 170 for display to a user. For example, a recommended pacing site using one of electrodes 144 in the LV may be determined automatically by IMD 10 using the techniques described herein and transmitted to programmer 170 for display to a user. Alternatively, programmer 170 may receive EGM signal data from IMD 10 and determine a recommended pacing site. In some embodiments, cardiac signal morphology analysis is performed to classify or identify pacing sites that are not recommended (non-recommended sites) to reduce the number of possible pacing sites from which a clinician must select from. For example if four pacing sites are tested, two may be classified as non-recommended sites based on EGM signal analysis. The other two remain unclassified or "available" candidate pacing sites which a clinician may choose from when programming a pacing vector for delivering a therapy.

Programmer 170 includes a display 172, a processor 174, a user interface 176, and a communication module 178 including wireless telemetry circuitry for communication with IMD 10. In some examples, programmer 170 may be a handheld device or a microprocessor-based home monitor or bedside programming device. A user, such as a physician, technician, nurse or other clinician, may interact with programmer 170 to communicate with IMD 10. For example, the user may interact with programmer 170 via user interface 176 to retrieve physiological or diagnostic information from IMD 10. A user may also interact with programmer 170 to program IMD 10, e.g., select values for operational parameters of the IMD. A user interacting with programmer 170 may request IMD 10 to perform a pacing site optimization algorithm and transmit results to programmer 170 or request data stored by IMD 10 relating to pacing site analysis procedures performed automatically by IMD 10 on a periodic basis. Processor 174 receives data from IMD 10 for use in generating a display presented on display 172 including information relating to recommended and/or non-recommended pacing sites.

Programmer 170 includes a communication module 178 to enable wireless communication with IMD 10. Examples of communication techniques used by system 100 include low frequency or radiofrequency (RF) telemetry, which may be an RF link established via Bluetooth, WiFi, MICS, or as described in U.S. Pat. No. 5,683,432 "Adaptive Performance-Optimizing Communication System for Communicating with an Implantable Medical Device" (Goedeke, et al). In some examples, programmer 170 may include a programming head that is placed proximate to the patient's body near the IMD 10 implant site, and in other examples programmer 170 and IMD 10 may be configured to communicate using a distance telemetry algorithm and circuitry that does not require the use of a programming head and does not require user intervention to maintain a communication link.

It is contemplated that programmer 170 may be coupled to a communications network via communications module 178 for transferring data to a remote database or computer to allow remote management of a patient using the techniques described herein. Remote patient management systems may be configured to utilize the presently disclosed techniques to enable a clinician to review cardiac signal data and authorize programming of IMD pace control parameters. For example, cardiac signals or parameters derived from cardiac signals may be transferred from programmer 170 to a clinic or other expert center for review. A recommended pacing site or pacing vector may be authorized for programming in the IMD by a clinician or other expert then programmed using remote IMD programming techniques via a communications network and programmer 170. Reference is made to commonly-assigned U.S. Pat. No. 6,599,250 (Webb et al.), U.S. Pat. No. 6,442,433 (Linberg et al.) U.S. Pat. No. 6,622,045 (Snell et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming, incorporated herein by reference in their entireties.

The techniques disclosed herein for classifying a pacing site may be performed during placement of leads 118, 120, and 122. For example, lead 120 may be positioned along LV 132, and an EGM morphology analysis is performed to evaluate the pacing sites of electrodes 144. If none of the locations of electrodes 144 are found to be recommended sites, the lead 120 can be repositioned and EGM morphology analysis may be repeated until a recommended site is identified. Additionally or alternatively, the EGM morphology analysis is performed after final placement of leads 118, 120 and 122 so that a best pacing site for achieving therapeutic benefit from CRT can be identified.

In some embodiments, external skin or surface electrodes 180, 182 and 184 may be placed on patient 114 for acquiring ECG signals during a pacing site selection procedure. Electrical conductors (not shown in FIG. 1 for the sake of clarity) connect ECG electrodes 180, 182, and 184 to programmer 170 to enable processor 174 to receive ECG signals and perform morphology analysis of the ECG signals for use in selecting a pacing site.

Figure 2:
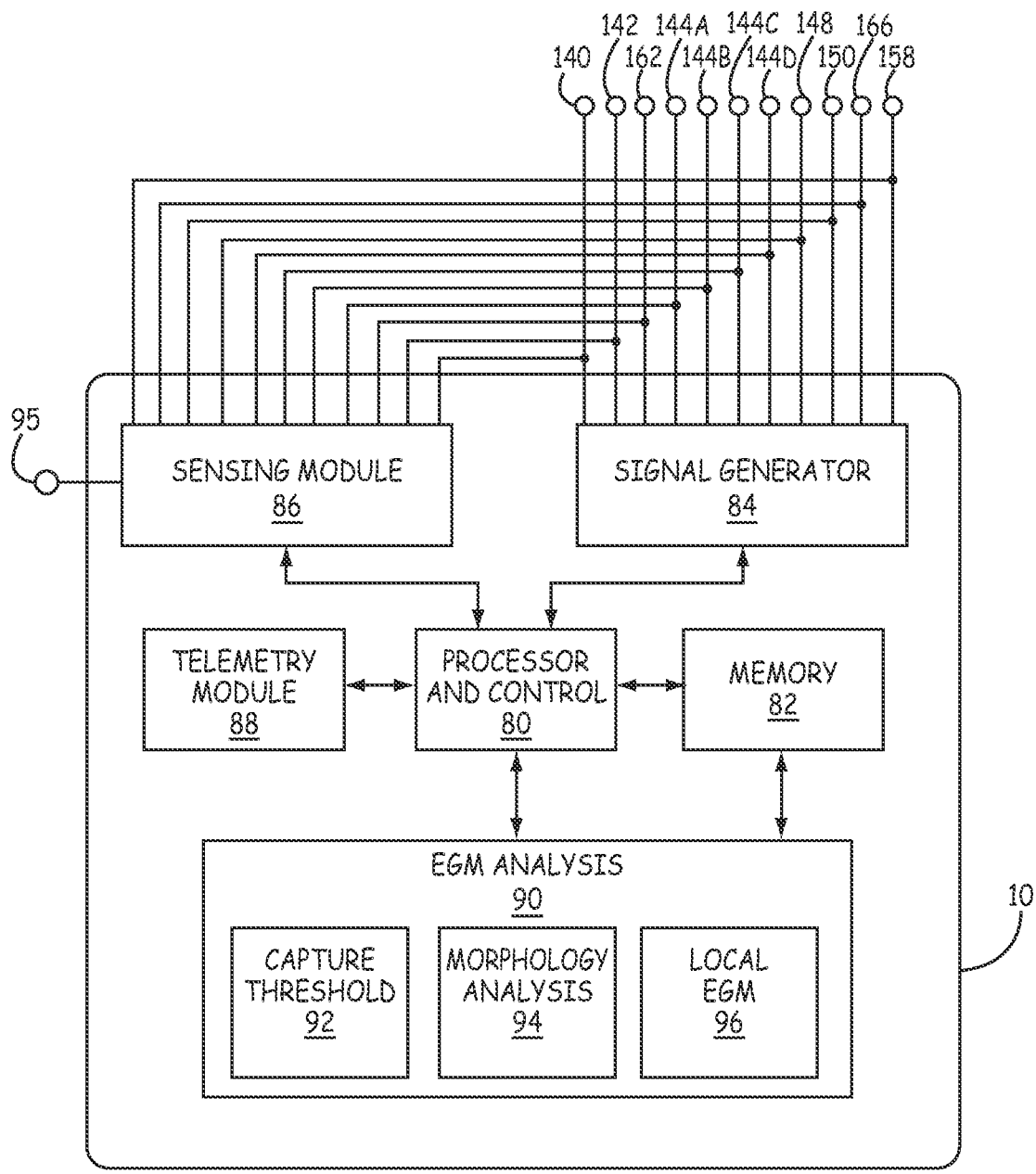
FIG. 2 is a block diagram illustrating one example configuration of the IMD shown in FIG. 1.

FIG. 2 is a block diagram illustrating one example configuration of IMD 10. In the example illustrated by FIG. 2, IMD 10 includes a processor and control unit 80, memory 82, signal generator 84, sensing module 86, and telemetry module 88. IMD 10 further includes EGM signal analysis module 90, which itself includes capture threshold detection module 92, morphology analysis module 94, and local EGM analysis module 96.

Memory 82 may include computer-readable instructions that, when executed by processor 80, cause IMD 10 and processor 80 to perform various functions attributed throughout this disclosure to IMD 10, processor 80, and EGM analysis module 90. The computer-readable instructions may be encoded within memory 82. Memory 82 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor and control unit 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, EGM analysis module 90 may, at least in part, be stored or encoded as instructions in memory 82 that are executed by processor and control 80.

Processor and control unit 80 includes a therapy control unit that controls signal generator 84 to deliver electrical stimulation therapy, e.g., cardiac pacing or CRT, to heart 112 according to a selected one or more therapy programs, which may be stored in memory 82. Signal generator 84 is electrically coupled to electrodes 140, 142, 144A-144D (collectively 144), 148, 150, 158, 162, and 166 (all of which are shown in FIG. 1), e.g., via conductors of the respective leads 118, 120, 122, or, in the case of housing electrode 158, via an electrical conductor disposed within housing 160 of IMD 10. Signal generator 84 is configured to generate and deliver electrical stimulation therapy to heart 112 via selected combinations of electrodes 140, 142, 144A-144D, 148, 150, 158, 162, and 166. Signal generator 84 is configured to deliver cardiac pacing pulses, which may be delivered according to atrial-ventricular (AV) and/or inter-ventricular (VV) timing intervals for delivering CRT.

Signal generator 84 may include a switch module (not shown) and processor 80 may use the switch module to select, e.g., via a data/address bus, which of the available electrodes are used to deliver pacing pulses. Processor 80 may also control which of electrodes 140, 142, 144A-144D, 148, 150, 158, 162, and 166 is coupled to signal generator 84 for delivering stimulus pulses, e.g., via the switch module. The switch module may include a switch array, switch matrix, multiplexer, or any other type of switching device suitable to selectively couple a signal to selected electrodes.

Sensing module 86 monitors signals from at least one of electrodes 140, 142, 144A-144D, 148, 150, 158, 162, or 166 in order to monitor electrical activity of heart 12. Sensing module 86 may also include a switch module to select which of the available electrodes are used to sense the cardiac activity. In some examples, processor 80 selects the electrodes that function as sense electrodes, or the sensing vector, via the switch module within sensing module 86.

Sensing module 86 includes multiple detection channels, each of which may be selectively coupled to respective combinations of electrodes 140, 142, 144A-144D, 148, 150, 158, 162, or 166 to detect electrical activity of a particular chamber of heart 112. Each detection channel may comprise an amplifier that outputs an indication to processor 80 in response to sensing of a cardiac depolarization, in the respective chamber of heart 112. In this manner, processor 80 may detect the occurrence of R-waves and P-waves in the various chambers of heart 12.

Sensing module 86 may further include digital signal processing circuitry for providing EGM analysis module 90 with digitized EGM signals. Alternatively, analog EGM signals may be provided to EGM analysis module 90 and digitized as needed for performing EGM morphology analysis.

Memory 82 stores intervals, counters, or other data used by processor 80 to control the delivery of pacing pulses by signal generator 84. Such data may include intervals and counters used by processor 80 to control the delivery of pacing pulses to one or both of the left and right ventricles for CRT. The intervals and/or counters are, in some examples, used by processor 80 to control the timing of delivery of pacing pulses relative to an intrinsic or paced event, e.g., in another chamber.

In one example, EGM analysis module 90 uses signals from sensing module 86 for use in classifying a pacing site. The capture threshold module 92 may be included to detect capture and/or loss of capture (LOC) when signal generator 84 delivers a pacing pulse. Capture threshold information may be used with morphology analysis information for producing an electrode site selection score. Via the switching module, processor 80 may control which of electrodes 140, 142, 144A-144D, 148, 150, 158, 162, and 166 is coupled to sensing module 86 to obtain EGM signals being analyzed for pacing site selection. Processor 80 may also control which of electrodes 140, 142, 144A-144D, 148, 150, 158, 162, and 166 is coupled to sensing module 86 to detect a local EGM signal which may additionally be used in some embodiments for selecting a pacing site.

Memory 82 may store predetermined morphology signal templates. In some examples, EGM signals are sensed during intrinsic cardiac rhythms for establishing baseline or control EGM templates. For example, an RV EGM signal template and an LV EGM signal template may be established. Parameters and equations for determining a matching score between a template and a newly acquired EGM signal may also be stored in memory 82. Thresholds or ranges for classifying or designating a pacing site as recommended, not recommended, acceptable or other designations may be stored in memory 82.

Processor 80 controls the selection of electrode configurations for delivering pacing pulses and for sensing EGM signals. Processor 80, for example, may communicate with signal generator 84 to select two or more stimulation electrodes in order to generate one or more pacing pulses for delivery to a selected chamber of heart 112. Processor 80 may also communicate with sensing module 86 to select two or more sensing electrodes for EGM signal acquisition and capture detection based on the chamber in which the pacing pulse is delivered by signal generator 84.

EGM analysis module 90, in the example of FIG. 2, is capable analyzing an EGM signal, for example using wavelet analysis as generally disclosed in U.S. Pat. No. 6,393,316 (Gillberg, et al). Other morphology analysis methods may be used, including determining one or more morphological features of the QRST waveform, such as an amplitude, slope, slew rate, area under the waveform, zero-crossing times, or the like. EGM analysis module 90 is further configured to compare the EGM morphology occurring during pacing at a test pacing site with a stored template. Based on this comparative analysis, the EGM analysis module 90 and/or processor 80 are configured to determine a pacing site selection score.

Using techniques of this disclosure, EGM analysis module 90 may determine a pacing site selection score for each of multiple pacing sites by, for each of the sites, delivering pacing pulses above a capture threshold, obtaining an EGM signal, and performing a comparative analysis of the EGM signal morphology with a stored EGM morphology template.

A capture threshold may be determined for each candidate pacing site. Numerous techniques may be implemented for measuring capture threshold. In one embodiment, the techniques disclosed in U.S. patent application Ser. No. 12/909,057 are implemented for measuring multiple pacing vector capture thresholds using a multipolar LV lead. U.S. patent application Ser. No. 12/909,057, filed on Oct. 21, 2010, and entitled "CAPTURE THRESHOLD MEASUREMENT FOR SELECTION OF PACING VECTOR", is commonly assigned and hereby incorporated herein by reference in its entirety.

During an EGM analysis procedure for identifying recommended pacing sites or alternatively identifying pacing sites that are not recommended, pacing pulses are delivered at a candidate pacing site. After a pacing pulse is delivered, sensing module 86 and EGM analysis module 90 obtain an EGM signal and determine an EGM morphology measurement. Processor 80 compares the morphology measurement to stored template measurements for classifying the pacing site. Alternatively, the sensing module 86 and EGM analysis module 90 determine a control EGM morphology measurement during no pacing at a candidate site then determines an EGM morphology measurement during pacing at a candidate site. While a control EGM measurement involves no pacing at a candidate site, for example at a candidate LV pacing site, pacing in another heart chamber may be performed during the control EGM morphology measurement, e.g. atrial pacing may be delivered with no pacing at a candidate LV pacing site to obtain a control EGM morphology measurement in the ventricles.

Local EGM analysis module 96 may optionally be provided for analyzing a local EGM signal obtained at a candidate pacing site to use in combination with a more distant or global EGM measurement, analyzed by morphology analysis module 94. A local EGM analysis provides information relating to the health of the local myocardial tissue, e.g. viable tissue, scar tissue, etc. A more distant or global EGM morphology analysis provides information relating to the synchronization or the ventricles. As such, in some embodiments, both a local EGM analysis and a relatively more global EGM morphology analysis may be performed in classifying a pacing site.

It is further contemplated that methods described herein may be implemented using a cardiac signal other than cardiac electrical signals attendant to the depolarization and repolarization of the heart tissue, i.e., EGM or ECG signals. For example, electrodes 140 through 166 may be used to acquire cardiac impedance signals. In other embodiments, another type of physiological sensor 95 is coupled to sensing module 86 and used for obtaining a cardiac signal that is not an electrical signal. Sensor 95 may be embodied as a mechanical, optical or other type of transducer, such as a pressure sensor, oxygen sensor, accelerometer, or any other sensor that is responsive to cardiac function and produces a cyclical signal corresponding to the cardiac cycle. A morphology comparison of the cyclical signal obtained from other types of cardiac signals could be used for the purpose of classifying pacing sites.

For example, intracardiac impedance may be measured using cardiac electrodes, such as electrodes 140, 142, 144, and 162 coupled to sensing module 86. The morphology of a continuous intracardiac impedance signal acquired during cardiac contraction could be used to compare pacing sites relative to a control morphology during no pacing in the heart chamber being evaluated. In another illustrative example, sensor 95 may be embodied as an accelerometer incorporated into a cardiac lead or sensor and the morphology of the accelerometer signal during pacing at a candidate pacing site may be compared to a control signal during no pacing at the candidate site to determine if the pacing site is a recommended, or alternatively a non-recommended, pacing site.

Figure 3:
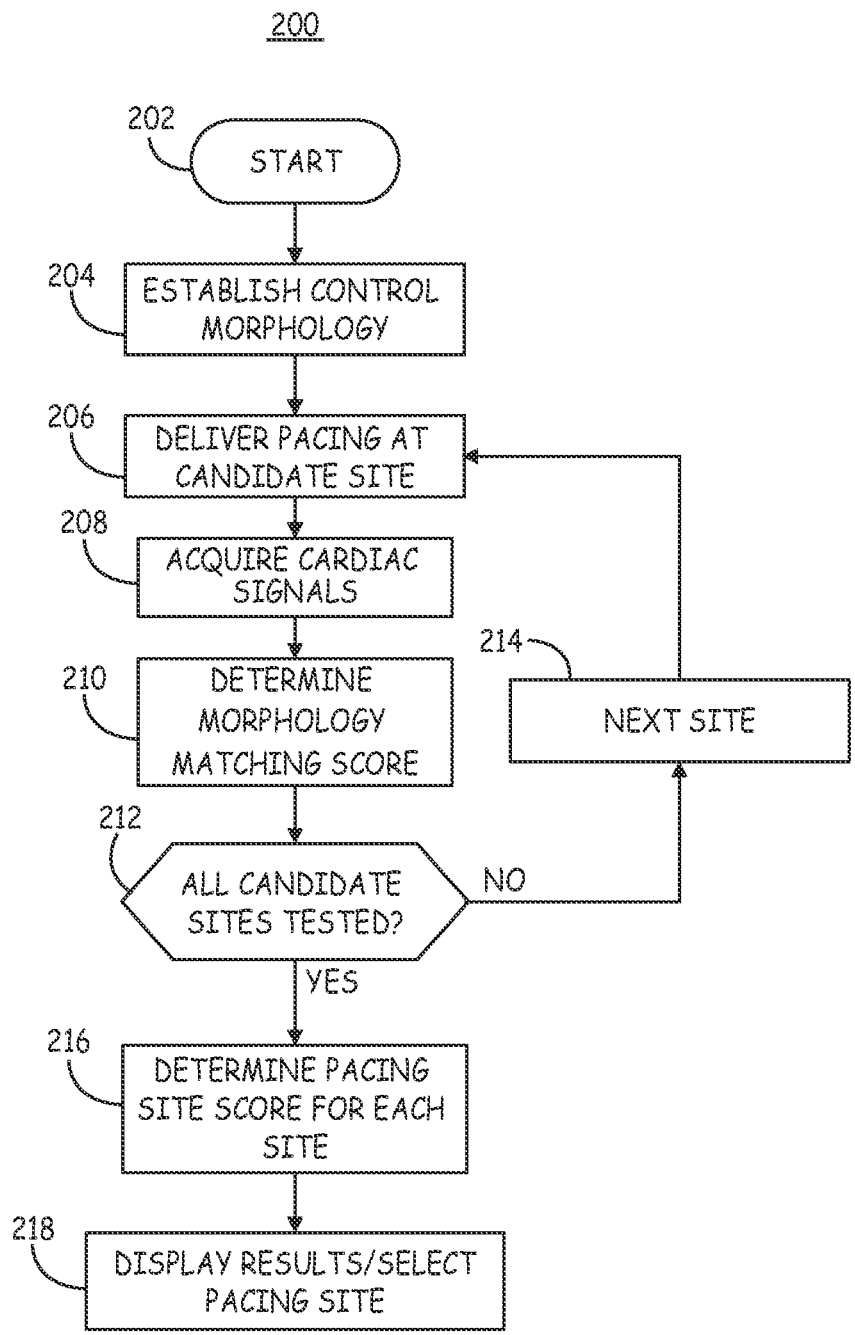
FIG. 3 is a flow chart of a method for classifying candidate pacing sites according to one embodiment.

FIG. 3 is a flow chart 200 of a method for classifying candidate pacing sites according to one embodiment. It is understood that methods described may be implemented using surface ECG electrodes for acquiring cardiac signals, which are subsequently processed and analyzed by an external processor. Alternatively, the methods may be implemented using implanted electrodes, such as the transvenous electrodes shown in FIG. 1, for acquiring cardiac signals, which are subsequently processed and analyzed by an implanted or external processor or a combination of both. In still other embodiments, cardiac impedance signals or other non-electrical cardiac signals may be used for performing morphological comparisons for facilitating pacing site selection.

Flow chart 200 and other flow charts presented herein are intended to illustrate the functional operation of the device, and should not be construed as reflective of a specific form of software or hardware necessary to practice the methods described. It is believed that the particular form of software, firmware, hardware or combination thereof will be determined primarily by the particular system architecture employed in the device and by the particular signal sensing and therapy delivery methodologies employed by the device. Providing software, firmware, and/or hardware to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The pacing site classification process is initiated manually or automatically at block 202. In one embodiment, the process is initiated upon user command using programmer 170 during a lead placement procedure for guiding placement of a cardiac lead. The process may alternatively be initiated by a user to guide selection of a pacing electrode vector from a multi-polar lead placed along a heart chamber, such as LV lead 120 shown in FIG. 1. In other embodiments, the process may be performed automatically by IMD 10 to maintain an optimal pacing site during therapy delivery when a multipolar lead is positioned in or along a heart chamber. The process may be performed periodically or in response to a change in a patient condition, indicating a need for therapy adjustment.

At block 204, a control morphology template is established. The control morphology template may include one or more measurements of morphological features for establishing a digitized template of the QRS waveform. The control morphology template is obtained when no pacing is delivered in a heart chamber for which pacing site selection is being performed. For example, if a pacing site in the LV is being selected during a lead placement procedure or during electrode selection from a multipolar LV lead, no LV pacing is delivered during the establishment of the control morphology template. In some embodiments, no ventricular pacing will be delivered such that an intrinsic QRS complex is used for establishing the control morphology template. Atrial pacing may or may not be provided to maintain a base heart rate during acquisition of cardiac signals used for establishing a control morphology template. In other embodiments, pacing in the opposite heart chamber may be delivered. For example, pacing may be provided at a selected RV pacing site when multiple candidate LV pacing sites are being tested or vice versa. As such, at block 204, no pacing may be delivered at all so that an intrinsic cardiac signal is obtained for establishing the control morphology template. Alternatively, pacing may be delivered in one or more heart chambers at block 204 but not in the chamber in which pacing site selection is being performed.

In still other embodiments, establishing a control morphology template may include storing a morphology template or template features established from clinical data. Instead of deriving a control template from the patient's own cardiac signals, clinically established template features of ECG or EGM waveforms may be stored in memory associated with a programmer enabled to perform the methods described. For example, a large number of CRT patients present left bundle branch block (LBBB). Particular ECG vectors present features typical of LBBB and useful in diagnosing LBBB. Such ECG features, or correlated EGM features, may be stored in memory associated with the processor performing the pacing site classification method, alone or in combination with an individual-patient derived control morphology template.

After establishing a control morphology template, pacing is delivered at a first candidate pacing site at block 206. Pacing is delivered at a suprathreshold pulse amplitude and pulse width to successfully capture the heart at the candidate pacing site. Timing intervals, such as an atrial-ventricular (AV) interval and/or inter-ventricular (VV) interval may be set to a minimal value or other default value used for all candidate pacing sites. Alternatively, timing intervals may be optimized for each candidate pacing site. Optimization of a timing interval may be based on Doppler echocardiography, e.g. maximal separation of E and A waves, or a greatest improvement in a hemodynamic measurement such as a maximum LV dP/dt or any other method for timing parameter optimization according to clinician preference.

At block 208, EGM or ECG signals, also referred to herein as "cardiac electrical signals" are acquired during pacing at the candidate site. The cardiac electrical signals may be acquired for one or more cardiac cycles and ensemble averaged or measurements of signal features taken from individual cardiac cycles may be averaged to obtain a morphology template corresponding to the candidate pacing site. The cardiac electrical signals may be sensed using surface ECG electrodes or any available implanted electrodes.

At block 210, a morphology matching score is determined by comparative analysis of the cardiac signal morphology during pacing at the candidate pacing site and the control morphology. In one embodiment, the morphology matching score is a percentage matching score determined by wavelet analysis. In another embodiment, morphology measurements, such as amplitude, slew rate, area under the waveform, etc., may be compared to determine a difference, percentage, ratio, or other metric of the relative difference between the control and test cardiac signal morphologies.

The processor and control unit selects the next candidate pacing site at block 214 and returns to block 206 to deliver pacing and determine a corresponding morphology matching score for the next candidate pacing site. Alternatively, a clinician may adjust a lead position to locate a pacing electrode at a new candidate pacing site. Two or more pacing sites may be evaluated. For example, using the quadripolar LV lead 120 shown in FIG. 1, four candidate sites may be evaluated corresponding to each of electrodes 144, which may be used in bipolar or unipolar configurations with each of electrodes 144A-144D selected one at a time as the cathode electrode selected with an anode. The anode used with a candidate cathode may be the same anode electrode used with all other candidate cathodes or a different anode electrode may be paired with each candidate cathode. For example, electrodes 144A-144D may be selected one at a time as a pacing cathode paired with the RV ring electrode 142, RV coil electrode 162, IMD housing 160, another of electrodes 144A-144D, or another available electrode as the pacing anode.

Once all candidate pacing sites to be tested have been used to deliver pacing pulses and corresponding morphology templates have been generated, as determined at block 212, a pacing site score is determined for each pacing site at block 216. A pacing site score is based on the morphology matching score. For example, threshold ranges or zones of a morphology matching score may be defined for assigning a pacing site score. When the control morphology template is based on an intrinsic rhythm or a paced rhythm when no pacing is delivered in the chamber for which a pacing site is being selected, the pacing site score has an inverse relation with the morphology matching score. The greatest change in the QRS morphology is desired when pacing is delivered at a candidate pacing site for achieving the greatest benefit from CRT. In other words, a pacing site associated with the greatest change in QRS morphology compared to the control template may be considered a recommended or acceptable pacing site. Perhaps more importantly, a pacing site with a high morphology matching score when compared with the control template is considered a non-recommended site and can be eliminated from pacing sites being considered. Elimination of pacing sites based on a high correlation with the control template results in a low pacing site score and narrows the available selection of candidate pacing electrode sites, making the selection of a pacing site easier for the clinician.

In an illustrative example, if a morphology matching score is 80% or greater, indicating a strong correlation between the candidate pacing site morphology and the control morphology, the candidate pacing site is not recommended; the pacing site score may be a "0". If the morphology matching score is 20% or less, indicating a low correlation between the candidate pacing site morphology and the control morphology, the pacing site score may be a "2" and is a recommended site. If the morphology score is greater than 20% but less than 80%, the pacing site may be considered acceptable and given a score of 1. The pacing site score may be assigned as a numerical value, a notation such as "recommended", "not recommended" or "acceptable", or may be indicated by color coding, such as red, yellow or green, on a display presented on programmer 170 for a clinician.

In some embodiments, a pacing site score may be combined with other pacing site selection considerations. For example, the pacing site score may be considered in combination with capture thresholds, local EGM analysis, the presence of inadvertent stimulation of non-cardiac tissue, presence of anodal capture, or other considerations taken into account when selecting a pacing site. An overall pacing site selection metric or score may be defined and computed as a weighted combination of the pacing site score, capture threshold, local EGM measurement or other pacing site selection considerations or any combination thereof.

At block 218, candidate pacing sites are classified, as described above, according to the pacing site score. The results may be displayed by programmer 170 (after transferring data from IMD 10 as needed). The programmer and/or IMD may automatically select a recommended pacing site and program the IMD to use the selected pacing site. In some embodiments, a list of classified pacing sites may be displayed by programmer 170 as recommended sites based on pacing site scores corresponding to a greatest morphological change from the control morphology template. Alternatively or additionally, a list of pacing sites that are not recommended may be displayed based on pacing site scores corresponding to the least morphological change from the control morphology template, i.e. highest morphology matching score indicating a small relative difference between the control and test morphologies. In some embodiments, a site that is not classified as "non-recommended" is not necessarily recommended since other factors may be taken into account in selecting a pacing site. As such, in some embodiments, pacing sites may be classified as non-recommended in response to a high morphology matching score and other pacing sites may be left unclassified in response to low morphology matching scores.

Figure 4:
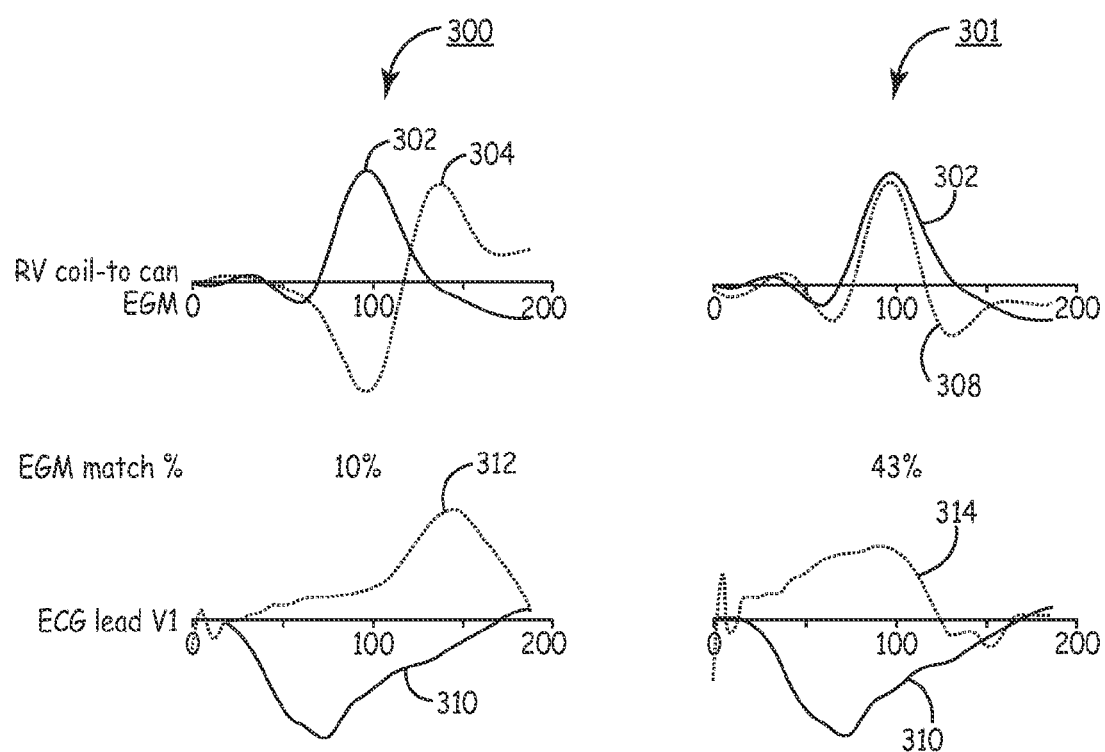
FIG. 4 is a depiction of cardiac signals recorded during LV pacing in a patient.

FIG. 4 is a depiction of cardiac signals 300 and 301 recorded during LV pacing in a patient. Cardiac signals 300 were recorded during pacing at a first candidate LV pacing site, and cardiac signals 301 were recorded during pacing at a second candidate LV pacing site. EGM signals 302, 304 and 308 were recorded between an RV coil electrode and the IMD housing electrode. EGM signal 302 is a control morphology template obtained during an intrinsic rhythm (no pacing).

EGM signals 304 and 308 are recorded during LV pacing at the two different candidate LV pacing sites using the same AV interval.

Signals 310, 312 and 314 are ECG lead V1 signals. ECG signal 310 is recorded during an intrinsic rhythm (no pacing). Signals 312 and 314 are recorded during LV pacing at the two candidate LV pacing sites.

An EGM morphology comparison using a wavelet analysis results in a morphology matching score of 10% for the first LV pacing site when the control EGM template 302 is compared to the LV paced EGM signal 304. A comparison between the control morphology template 302 and the LV paced EGM signal 308 yields a morphology matching score of 43% associated with pacing at the second candidate site. The lower morphology matching score associated with EGM signal 304 indicates the greatest difference in QRS morphology between the control (intrinsic) EGM signal 302 and a paced EGM signal 304 or 308. As such, the pacing site associated with EGM signal 304 is selected as a recommended pacing site out of the two candidate LV pacing sites being compared, or, alternatively, the pacing site associated with EGM signal 308, having the relatively highest morphology matching score, is classified as a non-recommended pacing site.

ECG recordings 310, 312 and 314 may be analyzed in an alternative embodiment and yield a similar result. A morphology matching analysis such as wavelet may be used or other signal features may be compared. For example, a difference between peak amplitudes, a difference between the time of the peak signal amplitude relative to a pacing pulse, or other signal differences between the control ECG morphology 310 and each of the paced ECG morphologies 312 and 314 may be measured. The comparison resulting in the greatest difference indicates the recommended pacing site, or, alternatively, the comparison resulting in the least difference indicates a non-recommended pacing site.

In this case, the patient is known to present ECG signals corresponding to LBBB. As such, a LV paced EGM signal may be compared to known LBBB morphology features to identify a LV pacing site which results in an EGM or ECG signal having the lowest correlation to a LBBB-type morphology, or to disqualify those pacing sites that have high correlation to an LBBB-type morphology. LBBB morphology metrics used for comparing to a paced cardiac signal morphology may be established from clinical data or from the patient's own intrinsic rhythm when the patient is known to present LBBB.

Figure 5:
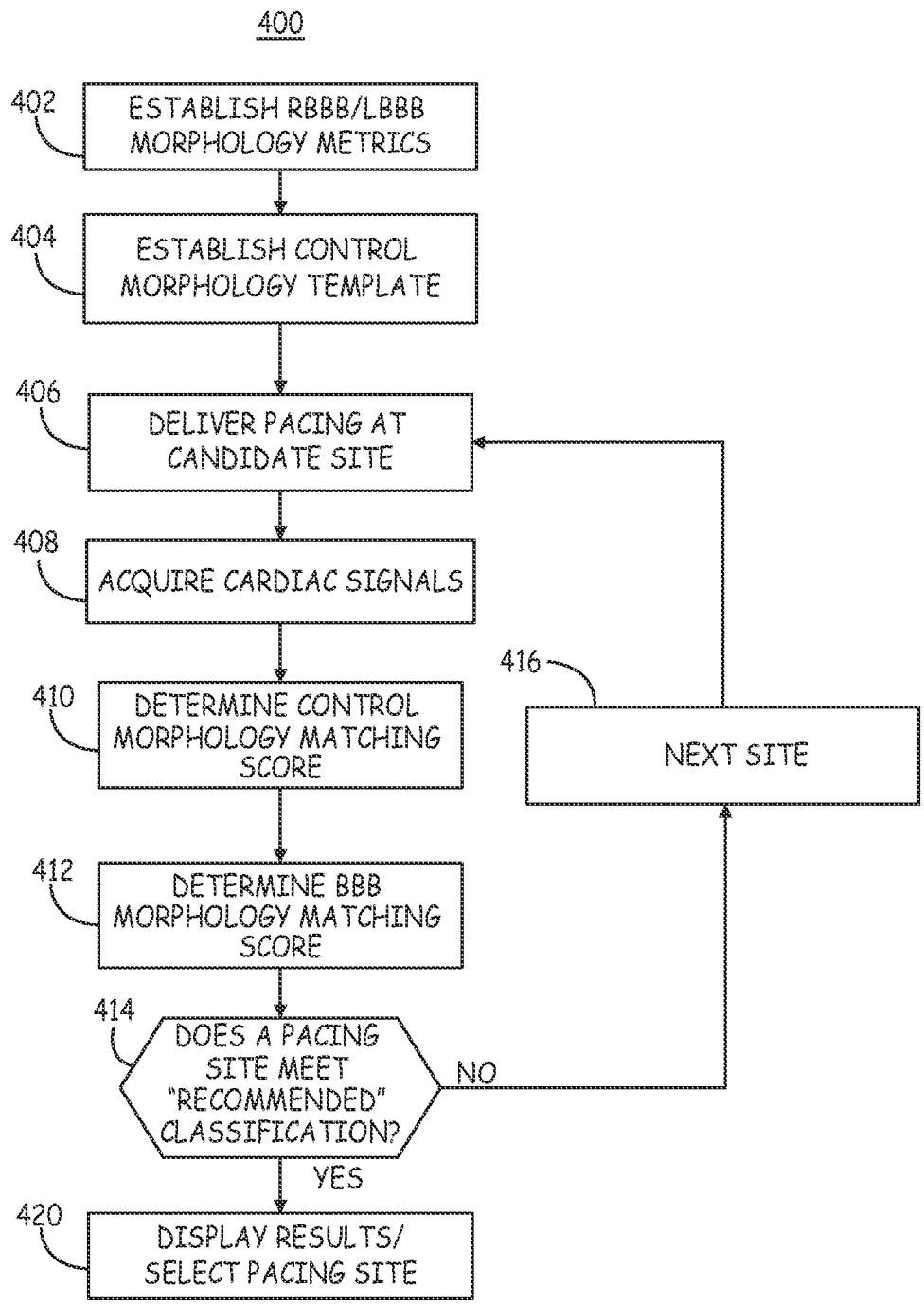
FIG. 5 is a flow chart of a method for selecting a pacing site according to an alternative embodiment.

FIG. 5 is a flow chart 400 of a method for selecting a pacing site according to an alternative embodiment. At block 402, morphology metrics corresponding to a bundle branch block (BBB) cardiac signal morphology are established. Morphology metrics corresponding to right bundle branch block (RBBB), LBBB or both may be established. BBB morphology metrics may be established using a patient's own intrinsic rhythm if the patient is known to present BBB. Alternatively, BBB morphology metrics may be established based on clinical knowledge. For example, a QS complex in ECG lead V1 with RSR' morphology in the left chest leads V5 or V6 is clinical evidence of LBBB. In RBBB, a leading deflection corresponding to the LV activation prior to RV activation may be seen such that there is an RSR' complex in right chest leads V1 or V2.

At block 404, the control morphology template is established in response to sensed cardiac signals during no pacing in the heart chamber for which pacing site selection is being performed. In some embodiments, two control morphology templates may be established, one for an intrinsic cardiac rhythm and one for an RV paced rhythm. A test morphology obtained during pacing at a candidate LV pacing site may then be compared to two control morphologies for identifying a pacing site that presents the greatest relative cardiac signal morphology change compared to both the two control morphologies.

Alternatively, if a predetermined pacing therapy involves LV pacing only, the control morphology template may be established during an intrinsic or atrial-only paced rhythm (no RV pacing). The LV pacing site for LV-only pacing is then classified based on a difference between a test morphology and an intrinsic or atrial-only paced control morphology. If a predetermined pacing therapy involves bi-ventricular pacing, the control morphology template may be established during RV pacing, with or without atrial pacing. A LV pacing site classification for biventricular pacing is then based on the difference between a test morphology and an RV-paced control morphology. An LV pacing site is classified as non-recommended based on a relatively smallest difference between the test morphology and the selected control morphology used for the comparative analysis (or classified as recommended based on the relatively largest difference between the test and control morphologies).

Pacing at a candidate site is initiated at block 406. Cardiac signals (e.g., EGM and/or ECG) are acquired at block 408 and processed at block 410 to determine a morphology matching score between the paced cardiac signal and the control morphology template(s).

At block 412, a matching score between the paced cardiac signal morphology and the established BBB morphology metrics is determined. In one example, a comparative score between an LV paced morphology and an established LBBB morphology metric is determined. A low correlation between the LV paced morphology and the LBBB morphology metric is desired. In another example, a comparative score between an LV paced test morphology and an established RBBB morphology metric is determined. A high correlation between the LV paced morphology and the RBBB morphology metric may be desired, for example during LV-only pacing.

At block 414, the processor determines whether the pacing site selection criteria are met for the candidate pacing site. If the pacing site selection criteria are not met, the process advances to block 416 to select a next candidate pacing site in the heart chamber. The process shown by flow chart 400 may be performed during lead placement in which case selection of the next candidate pacing site at block 416 may involve repositioning of an LV lead. If the LV lead is a multipolar lead, a different LV pacing electrode may be selected at block 416 as the cathode electrode for pacing in the LV.

Once an LV pacing site is identified which meets a "recommended" site classification, as determined at block 414, the process advances to block 420. Alternatively, if at least one pacing site is not classified as "non-recommended", the process may advance to block 420 to enable pacing site selection. If pacing site selection is to be performed in additional heart chambers, the process may return to block 416 where a candidate pacing site in another heart chamber is selected.

If process 400 is being performed during a lead placement procedure, pacing sites may be tested until a pacing site meets a "recommended" classification based on a pacing site score. Alternatively, pacing sites may be tested until at least one site is not classified as "non-recommended" when other classifications are not made. If process 400 is being performed after a lead has been implanted such that a selection is being made between existing electrode sites, all pacing sites may be tested and the pacing site identified having the greatest difference between the respective test and control morphologies is classified as the recommended site. Alternatively, a site having the lowest difference between its test morphology and the control morphology is classified as non-recommended. In other embodiments, sites having a difference below an acceptable threshold difference are classified as non-recommended or given a low pacing site selection score.

During pacing site classification in the LV, the comparison of the resulting cardiac signal morphology performed at block 412 involves a comparison with morphology metrics established for a RBBB morphology in one embodiment. During LV pacing, a maximum degree of RBBB-type morphology is desired. This type of morphology suggests propagation of the LV excitation wavefront toward the RV. If the merging excitation wavefronts occurring in the RV and in the LV are propagating in opposite directions during biventricular pacing, the highest increase in LV contractility may be achieved. If the directions of the advancing excitation wavefronts are not opposite, the activation of the ventricles is likely to be less synchronous. One way of achieving this maximum improvement in LV contractility during CRT may be to maximize a RBBB-type morphology during LV pacing and minimize the LBBB-type morphology to promote opposing excitation wavefronts in the RV and LV.

Accordingly, LV pacing site classification criteria may be established for requiring a low morphology matching score for the comparison between a test LV-paced morphology with the control morphology template and a high morphology matching score for the comparison with the RBBB morphology metric(s). As such, a correlation threshold may be predefined and applied to the morphology matching score obtained at block 410 for determining if the LV pacing site selection meets "recommended" classification criteria at block 414 relating to a low correlation with the intrinsic signal morphology. Additionally or alternatively, a correlation threshold for detecting a high correlation with a RBBB-type of morphology may be predefined and applied to the BBB morphology matching score (or to the LV paced cardiac signal directly) to determine if the LV paced morphology has a high correlation with a RBBB-type morphology.

If the LV paced morphology does not meet the "recommended" classification criteria, as determined at block 414, the LV lead may be repositioned or a different LV pacing electrode is selected at block 416 to evaluate a different candidate LV pacing site. Once a candidate pacing site is identified in the LV which meets the pacing site "recommended" criteria, the procedure is complete. In some embodiments, once a pacing site meeting "recommended" criteria is identified, the pacing site is selected as a recommended site and no additional candidate sites are tested. In other embodiments, multiple candidate sites are tested and the site achieving a highest pacing site selection score is selected as a recommended site.

Determining whether a pacing site meets "recommended" classification criteria at block 414 may include determining a pacing site selection score. The pacing site selection score may be a weighted combination of the result of the control morphology matching score and the BBB morphology matching score. For example, identification of a RBBB-type morphology during LV pacing may be given a "1". If a RBBB-type morphology is not identified during LV pacing at a candidate site, the site may be given a "0" for that portion of the pacing site score. Identification of a LBBB-type morphology during LV pacing may be given a "0", and low correlation with a LBBB-type morphology during LV pacing may be given a "1". The portion of the pacing site score corresponding to the control morphology matching score may be assigned as described above, e.g. if 20% or less a "2" is given and so on. As such, a best possible score for a candidate pacing site may be a "3". Alternatively, more weight may be given to the portion of the pacing site score corresponding to the control morphology matching score or to the portion corresponding to the BBB morphology matching score. The classification criteria may require a pacing site score of at least a 2 or at least a 3 to classify a candidate site as a recommended pacing site. A pacing site earning a score of 1 or less may be displayed as "not recommended".

The results may be displayed, e.g. in the form of a pacing site score, at block 420. For each of the candidate pacing sites tested, a pacing site score corresponding to the control morphology comparison and the BBB morphology comparison may be displayed, either separately or in a score that combines both the control and BBB morphology comparison results. A display presented to a clinician may include representative cardiac signals, such as shown in the example of FIG. 4, morphology matching scores, pacing site selection scores determined based on morphology matching scores or threshold comparisons, a "recommended" or "not recommended" annotation determined based on the pacing site selection scores, or any combination thereof.

In some embodiments, the IMD may perform the procedure shown by flow chart 400 by selecting candidate pacing sites from a multipolar lead positioned in a ventricular chamber. In this case, the IMD may automatically select a pacing site at block 420 in response to identifying a pacing site meeting "recommended" criteria. In other embodiments, the results for a candidate pacing site are displayed by the programmer to allow a clinician to select a pacing site by programming IMD using the programmer.

Figure 6:
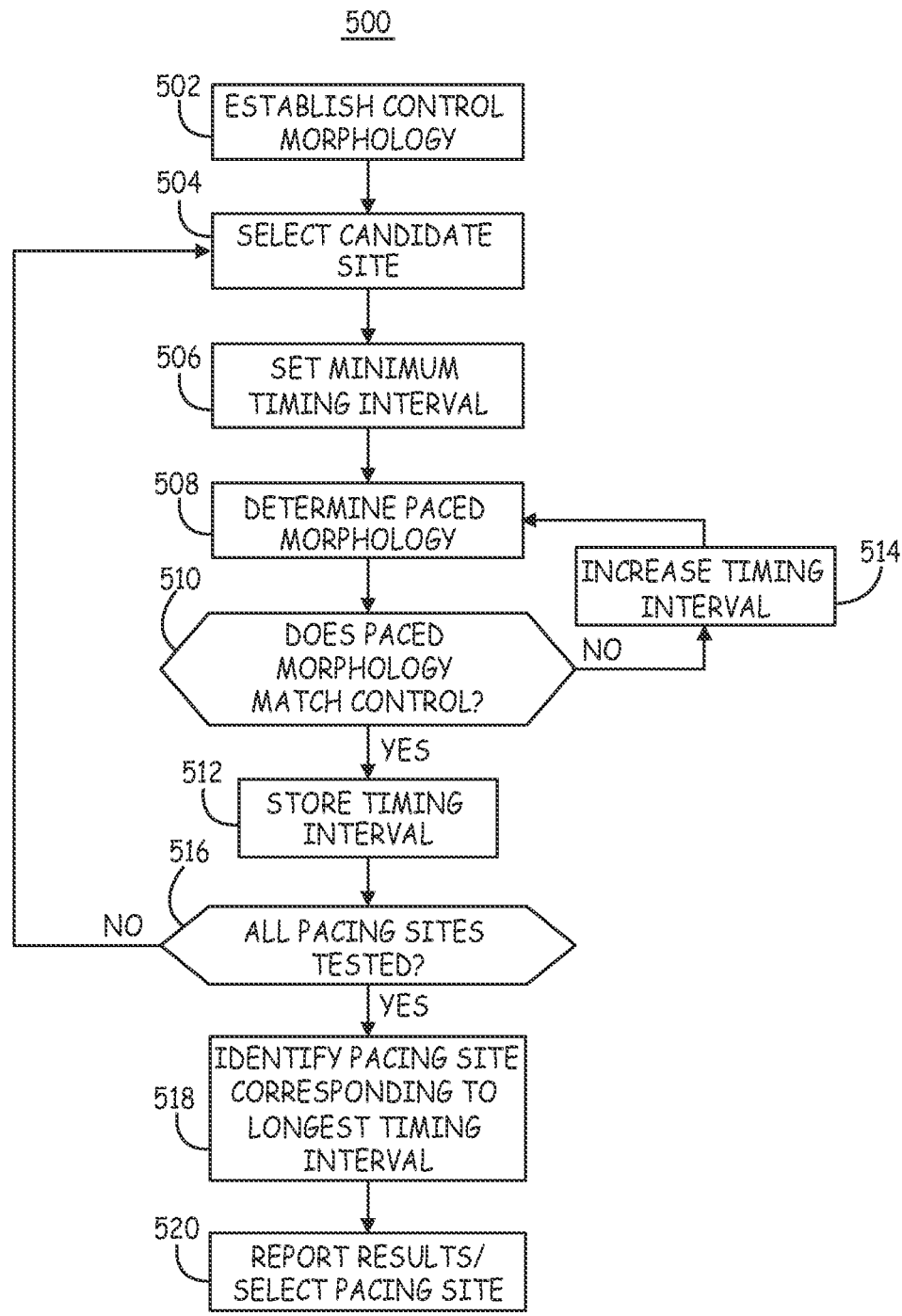
FIG. 6 is a flow chart of a method for selecting a pacing site according to yet another embodiment.

FIG. 6 is a flow chart 500 of a method for selecting a pacing site according to yet another embodiment. At block 502, a control morphology template is established during an intrinsic rhythm or during pacing that does not include pacing in the chamber for which pacing site selection is being performed. In an illustrative example, an LV pacing site is being selected. The control morphology may be established during an intrinsic rhythm or during atrial and/or RV pacing.

At block 504, a candidate pacing site is selected. A minimum timing interval controlling delivery of pacing pulses at the candidate site is set at block 506. The minimum timing interval is a VV interval in one embodiment such that the LV is paced at the shortest interval available relative to an RV pacing pulse or R-wave sensed in the RV. In other embodiments, the minimum timing interval may be set as a minimum AV interval defining the interval of time between an atrial paced or sensed event and the LV pacing pulse, with or without RV pacing.

At block 508, LV pacing is delivered at the candidate site at the minimum timing interval and the paced cardiac signal morphology is determined. The paced signal morphology is compared to the control morphology at block 510. If the paced morphology is different than the control morphology, as determined at decision block 510, the timing interval is increased at block 514. A detectable difference from the control morphology may be defined as some threshold difference in a morphology matching score or other comparative morphology measurement. A predefined threshold may be applied to a morphology matching score at block 510 to determine whether the paced morphology "matches" the control morphology. For example, a matching score of 80% or higher may be considered a match, though other thresholds may be used for determining an approximate match.

The timing interval continues to be increased at block 514 until the paced morphology substantially matches the control morphology. In other words, pacing is delivered at the candidate pacing site at increasing intervals of time until a pacing-induced change in the signal morphology is no longer present or detectable. The longest timing interval at which the pacing-induced morphology difference was still present is stored for the candidate pacing site at block 512.

If additional candidate pacing sites remain to be tested, as determined at decision block 516, the process returns to block 504 to select the next candidate site and reset the timing interval to a minimum value at block 506. The process then repeats to determine the longest timing interval at which a pacing-induced morphology change remains detectable (or outside some predefined matching threshold). Once all candidate pacing sites have been tested, the pacing site corresponding to the longest timing interval associated with a pacing-induced morphology change is identified as an optimal or recommended pacing site at block 518.

The results of the pacing site analysis may be reported and/or a recommended pacing site may be automatically selected at block 520. In some embodiments, the method shown by flow chart 500 may be combined with other methods described herein for classifying a pacing site or determining a pacing site selection score. For example, a portion of an overall pacing site selection score may be based on the time interval stored at block 512. The time interval may be determined as a percentage of the longest time interval stored for all candidate pacing sites associated with a pacing-induced morphology change. A recommended pacing site is associated with a longer time interval. As such, any pacing sites having a time interval percentage of 80% or more may be given a "2"; any pacing sites having a time interval percentage of less than 50% may be given a "0", and any pacing sites having a time interval percentage of 50% or more but less than 80% may be given a "1". This portion of the pacing site selection score may be combined with other pacing site selection score portions described herein, such as the control morphology matching score, BBB morphology matching score, capture threshold, presence or absence of undesired extra-cardiac stimulation, etc., in any weighted combination to obtain an overall site selection score. Alternatively, the time interval percentage or a score based thereon may be reported and displayed with other morphology-based pacing site analysis scores to enable a user to select an optimal pacing site.

Thus, a medical device system and associated methods have been presented in the foregoing description with reference to specific embodiments. It is appreciated that various modifications to the referenced embodiments may be made without departing from the scope of the disclosure as set forth in the following claims.

The invention claimed is:

1. A medical device for determining a pacing electrode site and delivering pacing pulses to a patient's heart, the device comprising:
 a plurality of electrodes for delivering pacing pulses to a patient's heart at a plurality of candidate cathode pacing electrode sites along a first heart chamber;
 a control unit operatively coupled with the plurality of electrodes for controlling the delivery of the pacing pulses, including selecting electrodes for delivering the pacing pulses to the plurality of candidate cathode pacing electrode sites selected one at a time;
 a sensing module for sensing a cardiac signal;
 a memory storing a first morphology template; and
 a processor configured to:
  receive the cardiac signal during pacing in the first heart chamber at each of the plurality of candidate cathode pacing electrode sites,
  for each of the plurality of candidate cathode pacing electrode sites determine a cardiac signal morphology in response to the cardiac signal and compare the determined cardiac signal morphology to a first morphology template, and
  classify each of the plurality of candidate cathode pacing electrode sites that result in greater than a threshold correlation between the cardiac signal morphology and the first template as a non-recommended pacing site for delivering a pacing therapy in the first heart chamber.

2. The device of claim 1, wherein the processor is further configured to determine the first morphology template in response to the sensed cardiac signal when no pacing pulses are being delivered in the first heart chamber.

3. The device of claim 2, wherein the first morphology template is determined during an intrinsic cardiac rhythm, the processor further configured to determine a second morphology template during pacing in a second heart chamber, compare determined cardiac signal morphology to the second morphology template and classify each of the plurality of candidate cathode pacing electrode sites in the first heart chamber in response to the comparing of the determined cardiac signal morphology to the first morphology template and the second morphology template.

4. The device of claim 1, wherein the processor is further configured to determine a morphology matching score in response to the comparing and to determine a pacing site score using the morphology matching score.

5. The device of claim 1, further comprising a memory storing an established bundle branch block morphology template, the processor configured figured to compare the determined cardiac signal morphology to the bundle branch morphology template, and classify each of the plurality of candidate cathode pacing electrode sites in the first heart chamber in response to the comparing of the determined cardiac signal morphology to the bundle branch block morphology template.

6. The device of claim 5, wherein the bundle branch block morphology corresponds to a right bundle branch block morphology, the memory stores a bundle branch block correlation threshold and a control morphology correlation threshold, and
 wherein the processor is further configured to classify each of the plurality of candidate cathode pacing electrode sites in the first heart chamber as a non-recommended site in response to the determined cardiac signal morphology being outside the bundle branch block correlation threshold of the right bundle branch block morphology and being within the control morphology correlation threshold of the first morphology template.

7. The device of claim 1, wherein the control unit controls delivery of pacing pulses at the plurality of candidate cathode pacing electrode sites along the first heart chamber, and wherein the processor is further configured to generate a determined cardiac signal morphology for each of the plurality of candidate cathode pacing electrode sites, determine a difference between each of the respective determined cardiac signal morphologies and the first morphology template and classify each of the plurality of candidate cathode pacing electrode sites, the classifying comprising classifying one of the plurality of candidate cathode pacing electrode sites corresponding to a greatest relative difference between a respective determined cardiac signal morphology and the first morphology template as a recommended site in the first heart chamber for delivering the pacing therapy to the first heart chamber and classifying one of the plurality of candidate cathode pacing electrode sites corresponding to a least relative difference between a respective determined cardiac signal morphology and the first morphology template as a non-recommended site in the first heart chamber for delivering the pacing therapy.

8. The device of claim 1, wherein the control unit controls delivery of pacing pulses at each of the plurality of candidate cathode pacing electrode sites at a plurality of pacing time intervals;

the processor is further configured to determine a cardiac signal morphology for each of the plurality of pacing timing intervals, compare each of the respective determined cardiac signal morphologies to the first morphology template, and for each of the plurality of candidate cathode pacing electrode sites determine a longest pacing time interval at which the respective determined cardiac signal morphology does not approximately match the first morphology template;

wherein classifying each of the plurality of candidate cathode pacing electrode sites in the first heart chamber comprises identifying one of the plurality of the candidate cathode pacing electrode sites that results in a longest one of the determined pacing time intervals as a recommended pacing site for delivering the pacing therapy in the first heart chamber.

9. The device of claim 1, wherein the processor is further configured to compute a pacing site score in response to the comparing, and further comprising a display for displaying the pacing site score to a user.

10. The device of claim 1, further comprising:
a memory storing an established morphology difference threshold; and
a display device,
wherein the control unit is configured to identify ones of the plurality of candidate cathode pacing electrode sites associated with a difference between the respective ones of the determined cardiac signal morphologies and the first morphology template that is less than the established morphology difference threshold, and wherein the identified ones of the plurality of candidate cathode pacing electrode sites are displayed on the display device as sites along the first heart chamber that are not recommended for selection as the pacing electrode site for delivering the pacing therapy in the first heart chamber.

* * * * *